United States Patent
Czapko (10) Patent No.: US 10,342,887 B1
(45) Date of Patent: Jul. 9, 2019

(54) THEFT RESISTANT AIR SCENTING DEVICE (71) Applicant: Raymond Czapko, Pittsburgh, PA (US)

(72) Inventor: Raymond Czapko, Pittsburgh, PA (US)

(73) Assignee: AirScent International, Pittsburgh, PA (US)

( * ) Notice: Subject to any disclaimer, the term of this patent is extended or adjusted under 35 U.S.C. 154(b) by 0 days.

(21) Appl. No.: 14/998,815

(22) Filed: Feb. 19, 2016

Related U.S. Application Data (60) Provisional application No. 62/176,487, filed on Feb. 19, 2015.

(51) Int. Cl.
*A61L 9/12* (2006.01)

(52) U.S. Cl.
CPC .............. *A61L 9/12* (2013.01); *A61L 2209/15* (2013.01)

(58) Field of Classification Search
CPC .............................. A61L 9/12; A61L 2209/15
USPC .............................. 239/327, 326, 328, 44, 45
See application file for complete search history.

(56) References Cited

U.S. PATENT DOCUMENTS

| | | | | |
|---|---|---|---|---|
| 4,722,477 A * | 2/1988 | Floyd | .................. | A01M 31/008 224/267 |
| 5,031,943 A * | 7/1991 | Scott | .................. | B65D 63/1081 24/16 PB |
| 5,621,949 A * | 4/1997 | Wells | .................. | B65D 63/1036 24/16 PB |
| 6,467,132 B1 * | 10/2002 | Robley | .............. | B65D 63/1018 24/16 PB |
| 2004/0083640 A1 * | 5/2004 | Harris | .................. | A01M 1/2044 43/1 |
| 2010/0212117 A1 * | 8/2010 | Haase | ................. | B65D 63/1027 24/16 PB |
| 2010/0236030 A1 * | 9/2010 | Dyer | .................... | B65D 63/1063 24/16 PB |
| 2010/0243826 A1 * | 9/2010 | West | ..................... | F16L 3/1041 248/68.1 |
| 2012/0286061 A1 * | 11/2012 | Ferree | .................. | A47K 5/1205 239/53 |
| 2014/0082923 A1 * | 3/2014 | Owen | ................. | B65D 63/1081 29/525.03 |

* cited by examiner

*Primary Examiner* — Arthur O. Hall
*Assistant Examiner* — Qingzhang Zhou
(74) *Attorney, Agent, or Firm* — Amad Tayebi; American Patent Associates (57) ABSTRACT

A washable theft resistant air scenting device is made of a hydrophobic impermeable flexible material which can absorb and desorb reversibly oil-base and/or solvent-base air scenting liquids. The device comprises an elongated member and a one way self-locking head having a through-opening adapted to receive the distal end of the elongated member and permit movement of the elongated member through the through-opening, only in one direction. Thus upon wrapping the elongated member around a stationary member and forming a closed loop around the stationary member, removal of the air scenting device would be difficult without destroying it.

9 Claims, 8 Drawing Sheets

Top View

Figure 1  Top View

Figure 2  Sectional View Q-Q

Figure 3

Figure 4 Top View

Figure 5 Sectional View A-A

THEFT RESISTANT AIR SCENTING DEVICE

I. CROSS REFERENCE TO A RELATED APPLICATION

This application claims benefit of provisional patent application, Ser. No. 62/176,487 titled "Air Scenting Device" and filed on Feb. 19, 2015. Provisional application No. 62/176,487 is incorporated herein, by reference, and in its entirety.

II. FIELD OF THE INVENTION

The present invention is in the field of air scenting devices. In particular, it teaches a washable theft-resistant air scenting device which, in addition to being suitable for other applications, is particularly suited for use in portable toilets.

III. BACKGROUND OF THE INVENTION

The prior art includes a variety of air scenting devices. Some prior art air scenting devices are used in public restrooms and, in most cases, are suspended on or attached to a wall at a high/hard to reach point in order to deter members of the public from removing them.

In portable toilets, however, the interior side walls are not sufficiently high to make it difficult, for members of the public, to reach and remove an air scenting device placed on the interior walls. Another problem encountered, when conventional air scenting devices are used in portable toilets, is that when the interior walls of a portable toilet are washed, the washing liquid splashes over the air scenting device, is absorbed by the air scenting device and damages the air scenting device.

The present invention addresses and solves both of the above-mentioned problems by providing air scenting devices which may be wrapped and locked around a stationary member (e.g., the vent pipe inside a portable toilet) thus making it difficult to remove the air scenting device without destroying it. Further, the air scenting device, of the present invention, is made of a water insoluble and non-absorbent material. In accordance with the present invention, elastomeric injection moldable pellets of Ethylene Vinyl Acetate copolymer (EVA), or other suitable materials are tumbled in a container containing an oil-base or a solvent-base air scenting liquid for a period of time, usually 24 hours. As a result of the soaked tumbling action, the pellets absorb an amount of air scenting liquid (about 25% of their dry weight). After injection molding of the air scenting liquid-saturated pellets in the form of an elongated member air scenting device, in accordance with the present invention, the air scenting device may be wrapped around a stationary member, inside the portable toilet, e.g., a vent pipe, and locked in place as taught in this disclosure. Also, since the EVA material and the absorbed oil or solvent are water insoluble, the air scenting device of the present invention makes it possible to wash portable toilets without damaging the air scenting devices mounted on their walls.

As may be concluded from the above, the present invention meets two portable toilet needs which have not been addressed, namely, deterring theft of the air scenting device and making it withstand the washing process without damage.

IV. DESCRIPTION OF COMPONENTS, ELEMENTS AND ACTIONS SHOWN IN THE DRAWINGS

Figure 5:
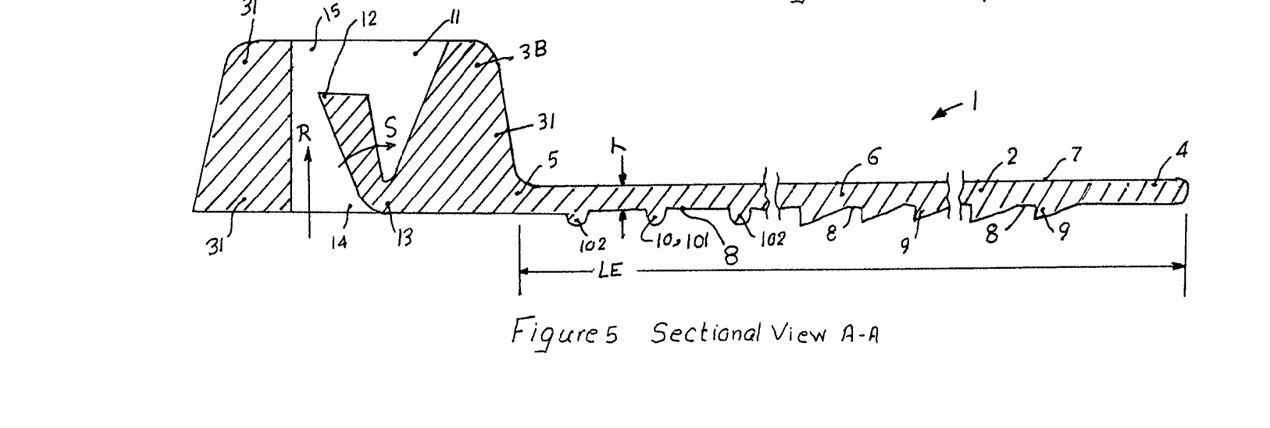
FIG. 5 shows a Front Sectional View A-A of air scenting device 1 shown in FIG. 4.
Figure 6:
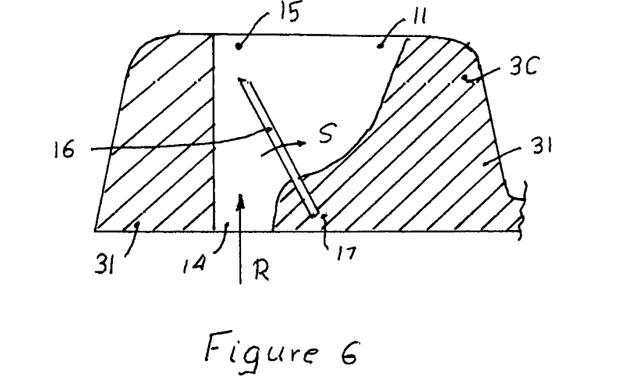
FIG. 6 shows a Sectional View of deflecting barb style one way self-locking head 3C.
Figure 7:
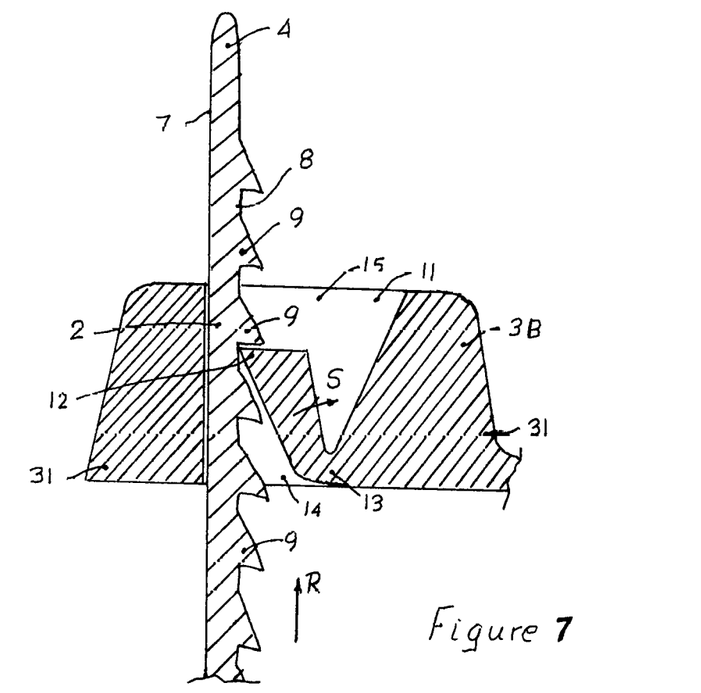
FIG. 7 shows a Sectional View of a deflecting pawl style one way self-locking head 3B engaging saw tooth like ridges 9 of elongated member 2.
Figure 8:
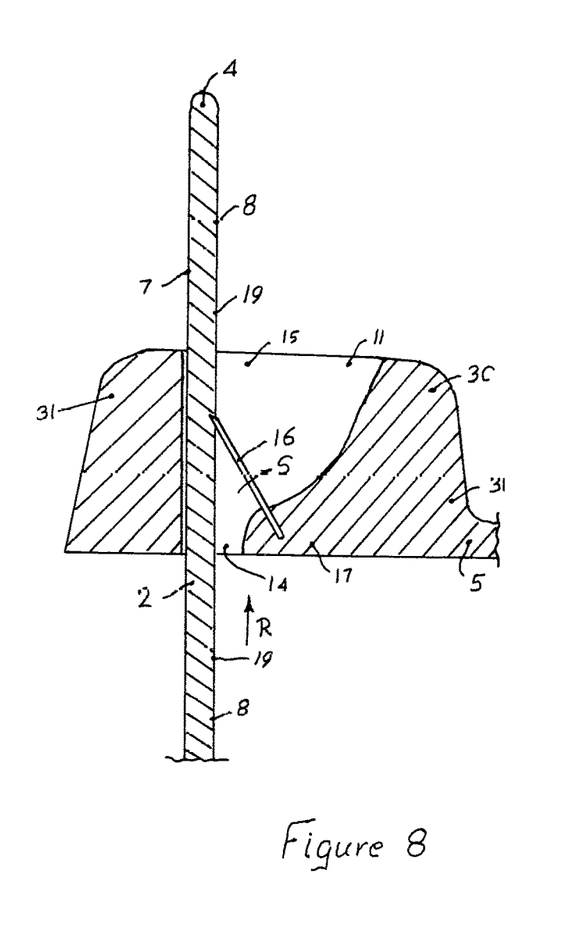
FIG. 8 shows a Sectional View of a deflecting barb style one way self-locking head 3C engaging planar surface 19 of inner surface 8 of elongated member 2.
Figure 9:
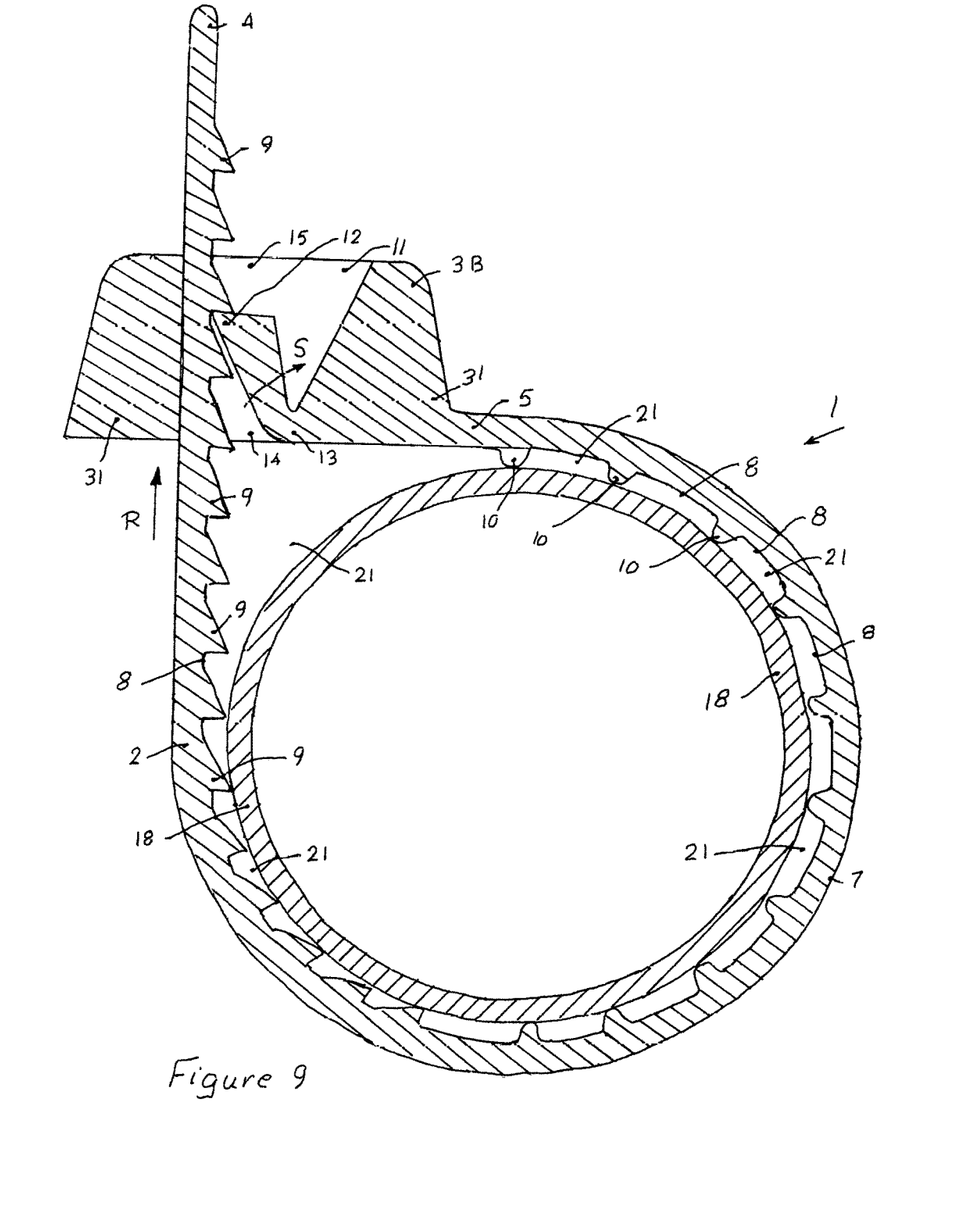
FIG. 9 shows a Top Sectional View of air scenting device 1, having a deflecting pawl style one way self-locking head 3B, wrapped around a stationary member (a vent pipe of a portable toilet).

A number of embodiments of the present invention, and their components, elements and/or actions are shown, in the drawings, and are identified, in the drawings, by the following alphanumeric references:

1: Embodiments of the air scenting device of the present invention.
2: Elongated member [strap].
3A: One way self-locking head; rectangular through-opening style.
3B: One way self-locking head; deflecting pawl style.
3C: One way self-locking head; deflecting barb style.
31: Body of one way self-locking head, 3A, 3B or 3C.
4: Distal, leading or insertion end of elongated member 2 [strap].
5: Proximal end of elongated member [strap] 2. End of elongated member joined to one way self-locking head 3A, 3B or 3C.
6: Body of elongated member 2.
7: Outer (Exposed) surface of elongated member 2.
8: Inner (Unexposed) surface of elongated member 2.
9: One way saw tooth-like ridges.
10: Spacers/projections/protrusions on unexposed surface 8.
101: Semispherical shape type spacers/projections/protrusions on unexposed surface 8.
102: Race track shape type spacers/projections/protrusions on unexposed surface 8.
11: Through-opening.
12: Deflecting pawl; permits only one way insertion and movement/travel of elongated member 2 through one way self-locking head 3B. Shown in monolithic/integral structure with body 31 of one way self-locking head, 3B. It deflects in direction S (as shown in FIGS. 5, 7 and 9) in order to permit elongated member 2 to travel through through-opening 11, only in direction R (as shown in FIGS. 5, 7 and 9) and recovers to engage one way saw tooth like ridge 9 and prevent intentional removal (including theft) of air scenting device 1 away from stationary member 18, shown in FIGS. 9 and 10, (such as vent pipe 18 in a portable toilet or any other stationary [rigidly held] member) around which elongated member 2 is wrapped, its leading end 4 is inserted through one way self-locking head 3B and tightened around stationary member 18.
13: Base of deflecting pawl 12.
14: Elongated member insertion end of through-opening 11.
15: Elongated member exit end of through-opening 11.
16: Deflecting barb; permits only one way insertion and movement/travel of elongated member 2 through one way self-locking head 3C. It is a metal strip embedded in body 31 of one way self-locking head 3C. It is insert molded in air scenting device 1. It deflects in direction S (see arrow in FIGS. 6 and 8) in order to permit elongated member 2 to travel through through-opening 11, (only in direction R, as shown in FIGS. 6 and 8) and elastically recovers to engage (chisel into) inner surface 8 of elongated member 2 in order to prevent intentional removal (including theft) of air scenting device 1 away from stationary member 18 or any other stationary (rigidly held) member around which elongated member 2 is wrapped, inserted through self-locking head 3C and tightened around stationary member [pipe] 18.
17: Holding base for deflecting barb 16.
18: Stationary member (for example a pipe or any other stationary [rigidly held] member such as the vent pipe of a portable toilet) around which elongated member 2 is wrapped, inserted through one way self-locking head 3A, 3B or 3C and tightened around stationary member 18.
19: Planar surface of inner surface 8.
20: Finger-size opening (through hole) to enable pulling and tightening elongated member 2 around stationary member 18.
21: Secondary/auxiliary air flow channels.

Figure 11:
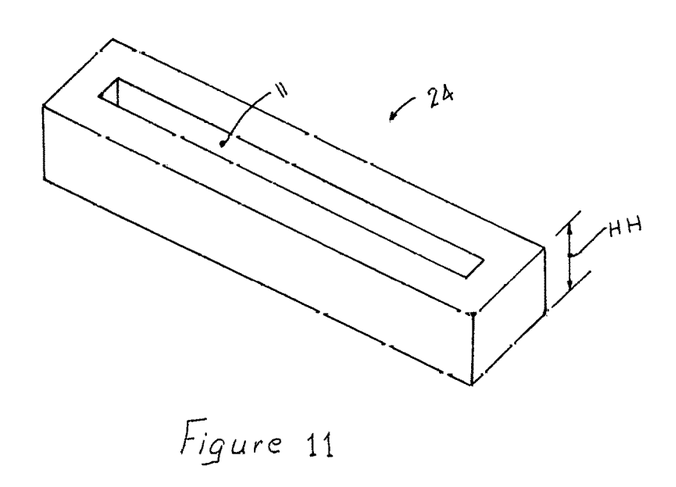
FIG. 11 shows an Isometric View of Locking Clip 24.

22: Space for logo, label, or any other product or product use-related information.
23: Vents (through vents), optional. Their use allows additional air flow through device 1 and increases the rate of evaporation of the air scenting liquid absorbed in air scenting device 1. Vents may be circular, as shown in FIG. 11, rectangular, oval, square, triangular or any other shape.
24: Locking clip, shown in FIG. 11. Made of a rigid material which is non-reactive with and non-absorbent of air scenting liquid absorbed in device 1, such as polypropylene and polyester. Its shape and dimensions are similar to one way self-locking head 3A, where its height HH (shown in FIGS. 2 and 11) is equal to and preferably slightly smaller than the distance between two successive ridges RS, shown in FIG. 2.
LO: Overall length of air scenting device 1.
LE: Effective length of elongated member 2.
T: Thickness of elongated member 2.
W: Width of elongated member 2.
RS: spacing between successive saw tooth-like ridges.
HH: Height of one way self-locking head; rectangular through-opening style, 3A. Also, Height of one way locking clip 24 (as shown in FIG. 11)
S: Direction of deflection of deflecting pawl 12 (as shown in FIGS. 5 and 7) and of deflecting barb 16 (as shown in FIGS. 6 and 8) upon insertion of distal end 4 of elongated member 2 through insertion end 14 of through-opening 11 of one way self-locking head 3B and 3C, respectively, and pushing elongated member 2 through the exit end 15 of through-opening 11.
R: Direction of travel of elongated member 2 through through-opening 11 of one way self-locking heads 3B and 3C.

V. SUMMARY OF THE INVENTION

With reference to FIGS. 1-11 and to the above Section IV titled "DESCRIPTION OF COMPONENTS, ELEMENTS AND ACTIONS SHOWN IN THE DRAWING", the present invention provides a novel air scenting device which is theft resistant (anti-theft) and waterproof and a novel method of air scenting.

In accordance with the present invention, an air scenting device 1 comprises;
an elongated member in the form of a strap, said elongated member having; a thickness, a width, an effective length, an outer surface, an inner surface, a dry mass, a distal end and a proximal end;
said proximal end terminating in and including a one way self-locking head, said one way self-locking head comprising a through-opening, said through-opening having an insertion end and an exit end, said insertion end being adapted to receive said distal end of said elongated member and to allow said elongated member to move through said through-opening and to exit through said exit end;
said effective length being sufficient to wrap said elongated member around a stationary member at least once;
at least one of said inner surface and said outer surface having saw tooth-like ridges aligned substantially parallel to direction of said width of said elongated member and oriented so as to enable insertion of said distal end through said insertion end and forward movement of said elongated member through said one-way self-locking head and to obstruct backward movement of said elongated member through said one way self-locking head;
said elongated member being made of a hydrophobic impermeable flexible plastic material which can absorb and desorb reversibly at least one of an oil-base liquid and a solvent-base liquid and being impregnated with at least one of an oil-base air scenting liquid and a solvent-base air scenting liquid and having an initial impregnated mass;
thereby, upon wrapping said elongated member around said stationary member and inserting said distal end into said insertion end of said through-opening and forwardly moving said elongated member through said exit end of said through-opening, thus irreversibly forming a continuous loop around said stationary member and thus forming a washable air scenting device resistant to removal without destroying it.

Other variants of the air scenting device of the present invention include the above-described air scenting device 1, wherein:
1) said flexible plastic material being ethylene vinyl acetate.
2) said one way self-locking head further comprising a deflecting pawl located between said insertion end and said exit end and shaped, positioned and oriented so as to prevent backward motion of said elongated member through said through-opening.
3) said deflecting pawl and said self-locking head forming a monolithic structure.
4) said one way self-locking head further comprising a metallic deflecting barb located between said insertion end and said exit end and shaped, positioned and oriented so as to prevent backward motion of said elongated member through said through-opening.
5) said elongated member comprising through holes.
6) at least one of said outer surface and said inner surface having protrusions.
7) the ratio of said initial impregnated mass to said dry mass being at least 1.25.
8) said elongated member being impregnated with essential oil.
9) said elongated member being made by injection molding.
10) subsequent to irreversibly forming a continuous loop around said stationary member, said distal end being inserted through and irreversibly engaging a rigid final locking clip.
11) said rigid final locking clip being made of inert material.
12) said rigid final locking clip being made of polypropylene.

VII. DESCRIPTION OF EMBODIMENTS OF THE INVENTION

Figure 1:
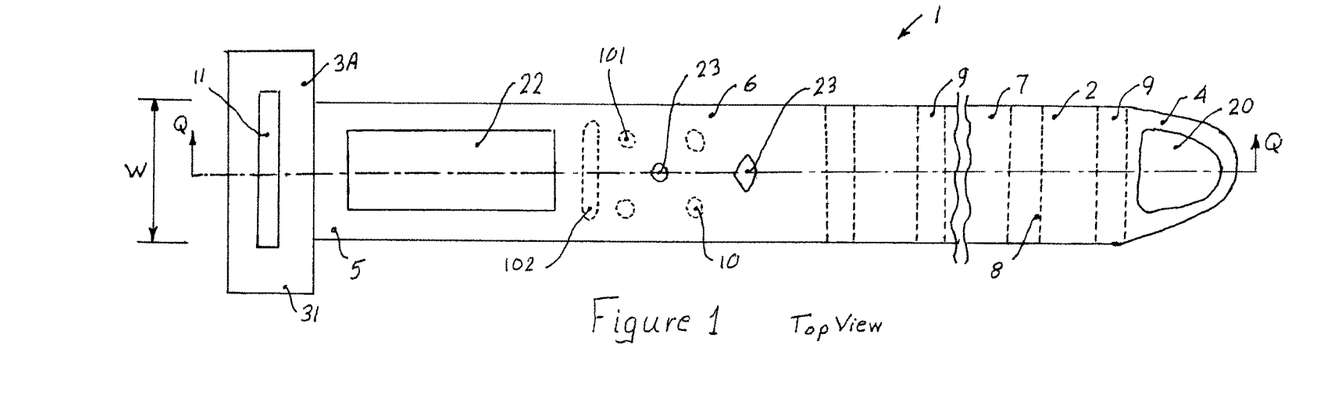
FIG. 1 shows a Top View of air scenting device 1, having a rectangular through-opening style one way self-locking head 3A.
Figure 2:
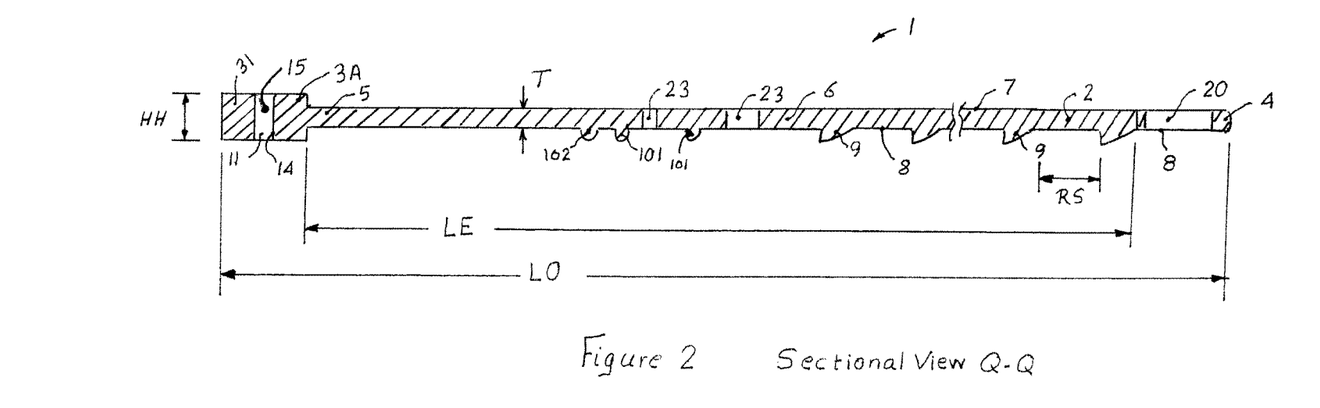
FIG. 2 shows a Front Sectional View Q-Q of air scenting device 1 shown in FIG. 1.
Figure 3:
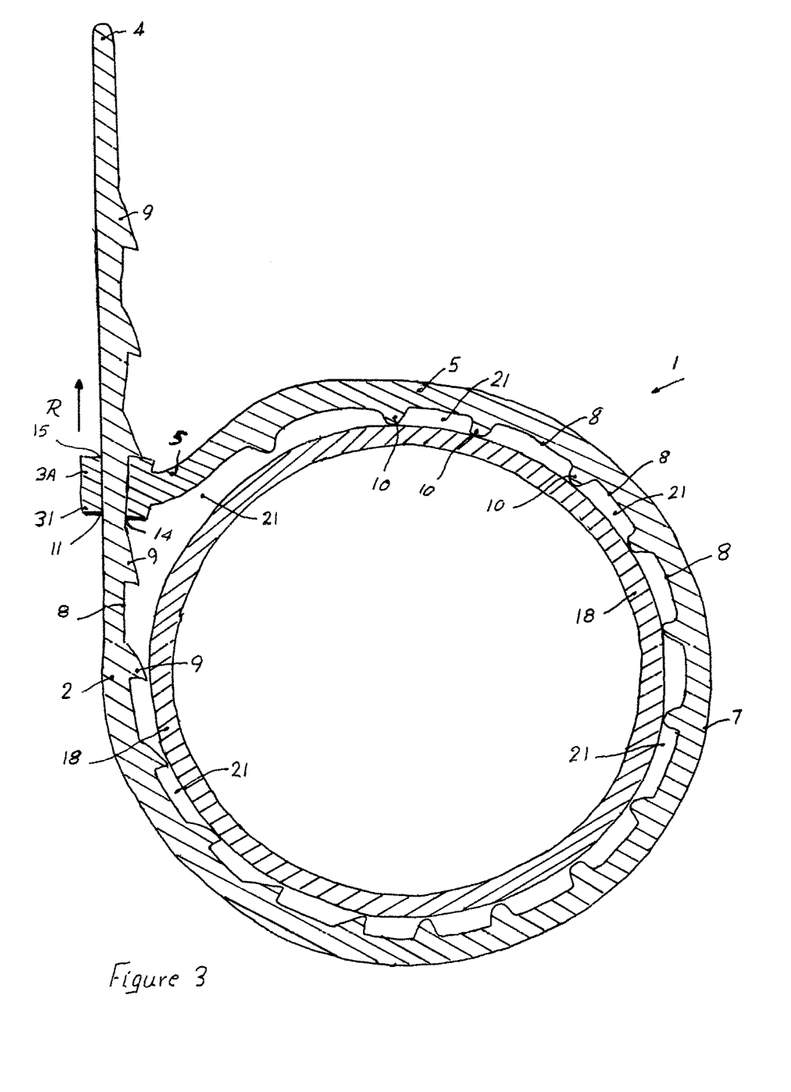
FIG. 3 shows a Top Sectional View of air scenting device 1, having a rectangular through-opening one way self-locking head 3A, wrapped around a stationary member (a vent pipe of a portable toilet).
Figure 4:
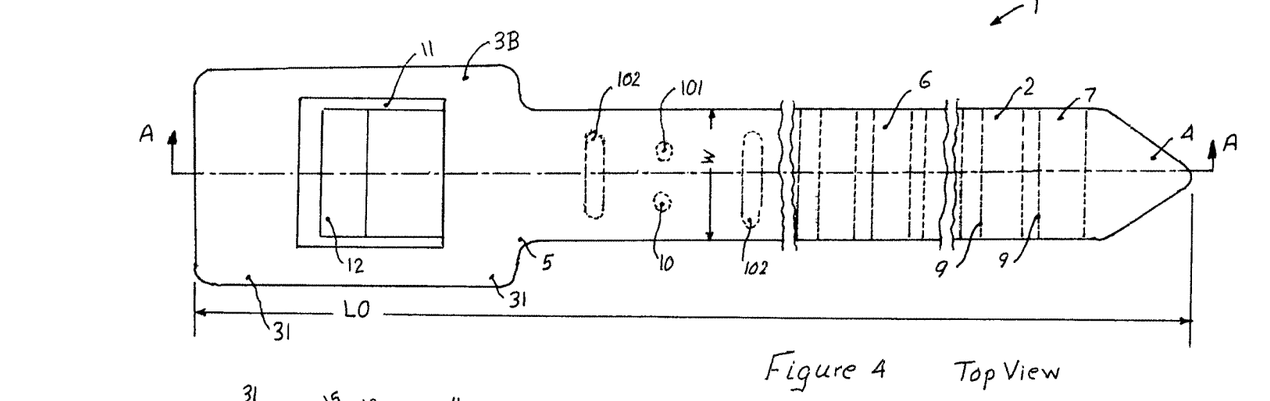
FIG. 4 shows a Top View of air scenting device 1, having a deflecting pawl style one way self-locking head 3B.
Figure 10:
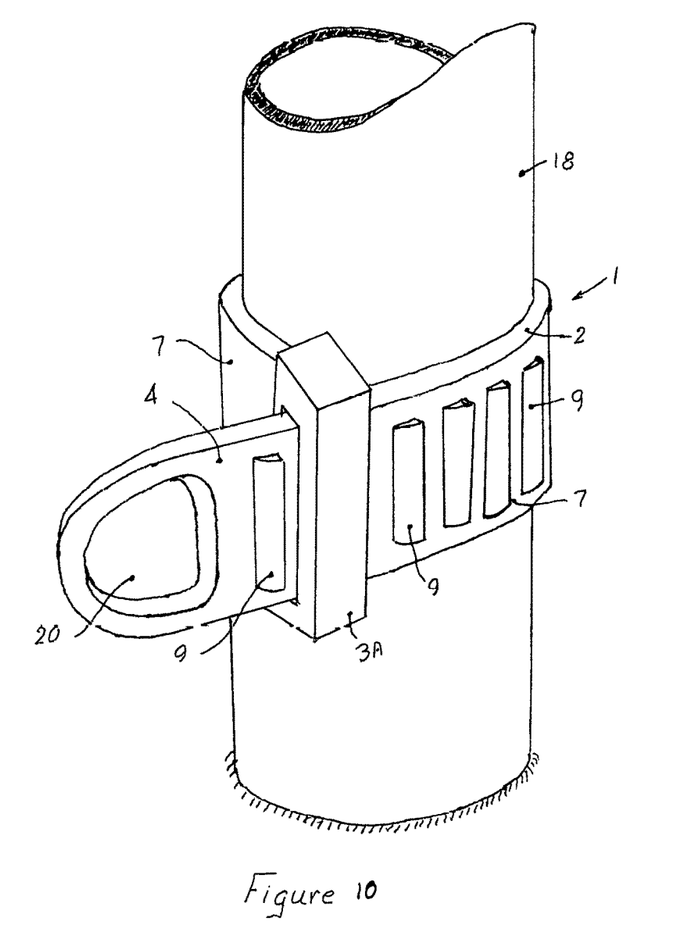
FIG. 10 shows an Isometric View of air scenting device 1, having a rectangular through opening style one way self-locking head 3A, wrapped around a stationary member (a vent pipe of a portable toilet).

FIG. 1 shows a top view and FIG. 2 shows a sectional view Q-Q of an embodiment of the air scenting device 1 of the present invention. As shown therein, air scenting device 1 comprises an elongated member 2 in the form of a strap. Elongated member 2 has an effective length LE, a proximal end 5, a distal end 4 and a body 6. The cross section of elongated member 2 may be of any shape, including circular, rectangular, square, race track or any other shape. In this embodiment, proximal end 5 terminates in and includes a one way self-locking head 3A. The overall length LO of device 1, in its initial (prior to use) state, is the effective length LE plus the length of self locking head 3A, measured in the same direction as the effective length LE. Elongated member 2 and self-locking head 3A are made of a hydrophobic impermeable flexible water-insoluble plastic material, such as EVA, which is impregnated with an oil-base or a solvent-base air scenting liquid. Similar materials are disclosed and described in U.S. Pat. Nos. 5,019,434 and 7,159,792, each of which is hereby incorporated in this application by reference and in its entirety. Self-locking head 3A has a body 31 which comprises a through-opening 11 adapted to receive distal end 4 of elongated member 2 and allow elongated member 2 to travel through said through-opening 11. Opening 11 has an elongated member insertion end 14 and an exit end 15. Through-opening 11 has a height HH which is equal to, or preferably slightly smaller than, the spacing RS between successive saw tooth like ridges 9 on inner surface 8 of elongated member 2, as shown in FIG. 2. Thus, upon wrapping said elongated member 2 around a stationary member 18 and insertion of distal end 4 of elongated member 2 into insertion end 14 of through-opening 11 and forwardly moving elongated member 2 through said through-opening 11 and exiting elongated member 2 through exit end 15 of through-opening 11, saw tooth like ridges 9 engage the exit end of through-opening 11 and form an irreversible loop around the stationary member 18, such as a vent pipe in a portable toilet, as shown in FIGS. 3 and 10. In order to further secure device 1 in its locked state around stationary member 18, a locking clip 24, shown in FIG. 11, may be similarly engaged with ridges 9 of elongated member 2.

In other embodiments, shown in FIGS. 4 to 9, one way self-locking head 3B has a through-opening 11 which includes, within its interior, a deflecting pawl 12, as shown in FIGS. 4, 5, 7 and 9 or, optionally, as shown in FIGS. 6 and 8, self-locking head 3C includes a deflecting barb 16) which permit only one way insertion and movement/travel of distal end 4 in direction R through opening 11 of self locking heads 3B and 3C.

Strap 2 has a strap body 6, an effective length LE, a width W and a thickness T. In a typical working embodiment of the air scenting device of the present invention, where the total initial impregnated weight of the device (weight before any evaporation of the air scenting liquid) is 60 grams, the overall length LO is 16 inches and the strap width W is 2 inches, the weight of the air scenting liquid contained within the plastic material is approximately 20% (12 gram), the device scents the interior air of a portable toilet for a period of about 60 days.

Strap 2 has an outer (exposed) surface 7 and an inner (unexposed) surface 8. In an embodiment of the present invention where through-opening 11 includes, within its interior, a deflecting pawl 12 (as shown in FIGS. 4, 5, 7 and 9) which permits only one way insertion and movement/travel of distal end 4 in direction R through opening 11 of self locking head 3B. Interior surface 8 has saw tooth like ridges 9 which, as distal end 4 of elongated member 2 is threaded through opening 11, push pawl 12 in direction S and rotate it around its base 13 in order to permit travel of strap 2 in direction R. As a ridge 9 escapes pawl 12, pawl 12 recovers back to its original position and prevents strap 2 from moving in a direction opposite to direction R, thus preventing intentional removal (including theft) of air scenting device 1 away from stationary member, (e.g., pipe 18 or any other stationary (rigidly held) member) around which strap 2 is wrapped and inserted through self-locking head 3B.

In order to help increase the rate of evaporation of air scenting liquid contained within strap body 6, unexposed surface 8 may be adapted to have spacers/projections 10, 101 and 102. As elongated member 2 is wrapped around stationary member 18, spacers 10 create secondary/auxiliary air flow channels 21 between inner surface 8 and the exterior surface of stationary member 18, thus allowing/causing an increased rate of evaporation of the air scenting liquid. Spacers 10 may be of a semispherical shape (101) an elongated shape (102) or any other shape.

FIGS. 6 and 8 shows sectional views of self locking head 3C where opening 11 includes a metal strip barb 16 embedded (or insert-molded) in holding base 17 of body 31 of self-locking head 3C. As shown in FIG. 8, bard 16 permits only one way insertion and movement/travel of strap 2 through self-locking head 3C as it deflects in direction S (see arrow) in order to permit strap 2 to travel through opening 11, (only in direction R) and elastically recovers to engage (chisel into) inner surface 8 of strap 2 in order to prevent intentional removal (including theft) of air scenting device 1 away from stationary member, pipe 18 or any other stationary (rigidly held) member, around which strap 2 is wrapped and inserted through self-locking head 3C. In this embodiment of the present invention, inner surface 8 does not need to have saw tooth like ridges. Instead, inner surface 8 may have a planar surface 19, as shown in FIG. 5.

In order to make it easier to tighten the wrapping action of air scenting device 1 around stationary member 18, distal end 4 may be adapted to have a finger size opening 20, as shown in FIGS. 1, and 10.

Also, as shown in FIG. 1, outer surface 7 of elongated member 2 may be adapted to include a space 22 for logo, label or any other product or product use related information.

In accordance with the present invention, a method of scenting air comprises the steps of;
providing an air scenting device as described above, and wrapping said air scenting device around a stationary member as described above.

The invention claimed is:

1. A washable theft-resistant air scenting device comprising; an elongated member in the form of a strap, said elongated member having; a thickness, a width, an effective length, an outer surface, an inner surface, a dry mass, a distal end and a proximal end; said proximal end terminating in and including a one way self-locking head, said one way self-locking head comprising a through-opening, said through-opening having an insertion end and an exit end, said insertion end being adapted to receive said distal end of said elongated member and to allow said elongated member to move through said through-opening and to exit through said exit end; said distal end comprising a finger-size through hole in order to enable pulling and tightening said elongated member around a stationary member, said one way self-locking head having a height HH, said effective length being sufficient to wrap said elongated member around a said stationary member at least once; at least one of said inner surface and said outer surface having saw tooth-like ridges aligned substantially parallel to direction of said width of said elongated member and oriented so as to enable insertion of said distal end through said insertion end and forward movement of said elongated member through said one-way self-locking head and to obstruct backward movement of said elongated member through said one way self-locking head; said saw tooth-like ridges having a spacing RS between successive ridges, said elongated member being made of a hydrophobic impermeable flexible plastic material which can absorb and desorb reversibly at least one of an oil-base liquid and a solvent-base liquid and being impregnated with at least one of an oil-base air scenting liquid and a solvent-base air scenting liquid and having an initial impregnated mass; said theft-resistant air scenting device further comprising; a locking clip made of a rigid material which is non-reactive with and non-absorbent of air scenting liquid absorbed in said device, such as polypropylene and polyester, wherein shape and dimensions of said locking clip being similar to said one way self-locking head, and wherein its height HH being equal to said distance RS between successive ridges, thereby, upon wrapping said elongated member around said stationary member and inserting said distal end into said insertion end of said through-opening and forwardly moving said elongated member through said exit end of said through-opening, thus irreversibly forming a continuous loop around said stationary member and thus forming said washable air scenting device resistant to removal without destroying said washable air scenting device.

2. The air scenting device in accordance with claim 1, wherein said flexible plastic material being ethylene vinyl acetate.

3. The air scenting device in accordance with claim 1, wherein said elongated member comprising through holes.

4. The air scenting device in accordance with claim 1, wherein at least one of said outer surface and said inner surface having protrusions.

5. The air scenting device in accordance with claim 1, wherein the ratio of said initial impregnated mass to said dry mass being at least 1.25.

6. The air scenting device in accordance with claim 1, wherein said elongated member being impregnated with essential oil.

7. The air scenting device in accordance with claim 1, wherein said elongated member being made by injection molding.

8. The air scenting device in accordance with claim 1, wherein, subsequent to irreversibly forming said continuous loop around said stationary member, said distal end being inserted through and irreversibly engaging a rigid final locking clip.

9. The air scenting device in accordance with claim 8, wherein said rigid final locking clip being made of an inert material.

* * * * *